US012151238B2

(12) United States Patent
Samproni

(10) Patent No.: US 12,151,238 B2
(45) Date of Patent: Nov. 26, 2024

(54) LIQUID SENSOR ASSEMBLIES, APPARATUS, AND METHODS

(71) Applicant: Siemens Healthcare Diagnostics Inc., Tarrytown, NY (US)

(72) Inventor: Jennifer Samproni, Braintree, MA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 526 days.

(21) Appl. No.: 17/594,538

(22) PCT Filed: Apr. 9, 2020

(86) PCT No.: PCT/US2020/027362
§ 371 (c)(1),
(2) Date: Oct. 21, 2021

(87) PCT Pub. No.: WO2020/222990
PCT Pub. Date: Nov. 5, 2020

(65) Prior Publication Data
US 2022/0212187 A1    Jul. 7, 2022

Related U.S. Application Data

(60) Provisional application No. 62/839,827, filed on Apr. 29, 2019.

(51) Int. Cl.
*G01N 27/327*    (2006.01)
*B01L 3/00*    (2006.01)
*G01N 27/416*    (2006.01)

(52) U.S. Cl.
CPC ...... *B01L 3/502715* (2013.01); *G01N 27/327* (2013.01); *G01N 27/416* (2013.01);
(Continued)

(58) Field of Classification Search
CPC ......... B01L 3/502715; B01L 2200/025; B01L 2300/0634; B01L 2300/0663; B01L 2300/0816; G01N 27/327; G01N 27/416
See application file for complete search history.

(56) References Cited

U.S. PATENT DOCUMENTS 5,520,787 A * 5/1996 Hanagan ................ C12Q 1/001
                                                          435/287.7
6,096,275 A * 8/2000 Greenberg ......... G01N 33/4915
                                                          422/504
(Continued)

FOREIGN PATENT DOCUMENTS

EP        0102042 A2 *  3/1984  ............. G01N 27/30
WO     2016044417 A2     3/2016

OTHER PUBLICATIONS

International Search Report and Written Opinion of International Application No. PCT/US2020/027362 dated Jul. 17, 2020.

*Primary Examiner* — Alexander S Noguerola

(57) ABSTRACT

Disclosed is a sensor assembly including a flow channel; two or more working electrodes located in the flow channel; and one or more reference electrodes located in the flow channel, wherein a total number of working electrodes is greater than a total number of reference electrodes. Volume in the flow channel may be minimized Liquid testing apparatus and methods of testing test liquids are provided, as are other aspects.

20 Claims, 7 Drawing Sheets

(52) U.S. Cl.
CPC .  *B01L 2200/025* (2013.01); *B01L 2300/0645* (2013.01); *B01L 2300/0663* (2013.01); *B01L 2300/0816* (2013.01)

(56) References Cited

U.S. PATENT DOCUMENTS

| | | | |
|---|---|---|---|
| 6,123,820 A * | 9/2000 | Bergkuist | G01N 33/4915 |
| | | | 204/411 |
| 7,394,263 B2 | 7/2008 | Pechstein et al. | |
| 8,343,332 B2 | 1/2013 | Brown | |
| 8,652,313 B2 * | 2/2014 | Kobayashi | G01N 27/333 |
| | | | 204/411 |
| 8,702,933 B2 | 4/2014 | Ishige et al. | |
| 8,728,288 B2 | 5/2014 | Aas et al. | |
| 2007/0227885 A1 | 10/2007 | Okada et al. | |
| 2010/0121490 A1 | 5/2010 | Hongo et al. | |
| 2011/0279130 A1 | 11/2011 | Reccius et al. | |
| 2013/0199944 A1 | 8/2013 | Petisee | |
| 2013/0266979 A1 | 10/2013 | Segerink et al. | |
| 2018/0275088 A1 | 9/2018 | Huff et al. | |

* cited by examiner

LIQUID SENSOR ASSEMBLIES, APPARATUS, AND METHODS

This application claims priority to U.S. provisional application No. 62/839,827, filed Apr. 29, 2019, the disclosure of which is incorporated herein by reference in its entirety.

FIELD

The present disclosure relates to test sensors and sensing methods, and particularly to test sensor assemblies configured to test for a presence of one or more constituents within a test liquid, such as in a biological liquid specimen (bio-liquid specimen).

BACKGROUND

In liquid testing, such as in analyte testing of a bio-liquid specimen, a volume of a test liquid (e.g., whole blood, blood serum, or blood plasma) can be provided in a pathway and sensors contained in the pathway can be used to sense certain identifiable constituents contained in the bio-liquid specimen.

SUMMARY

Some embodiments of the present disclosure provide a sensor assembly configured to sense the presence of one or more constituents within a bio-liquid specimen.

Some embodiments of the present disclosure provide a sensor assembly configured to measure an amount of one or more analytes contained in a bio-liquid specimen obtained from a patient, wherein the available test liquid volume is very small, such as less than 100 µL, or even less than 50 µL in some embodiments.

Some embodiments of the present disclosure provide a sensor assembly configured to sense the presence of one or more constituents within a bio-liquid wherein the sensor assembly includes a single reference electrode.

Some embodiments of the present disclosure provide a sensor assembly wherein the sensor assembly includes more working electrodes than reference electrodes, not in a 1:1 ratio.

Embodiments of the present disclosure provide a sensor assembly configured to minimize an amount of test liquid (e.g., bio-liquid specimen) used therein. The sensor assembly comprises a flow channel; two or more working electrodes located in the flow channel; and one or more reference electrodes located in the flow channel, wherein a total number of working electrodes is greater than a total number of reference electrodes.

In a system aspect, a liquid testing apparatus is provided. The liquid testing apparatus comprises a flow channel; two or more working electrodes located in the flow channel; and one or more reference electrodes located in the flow channel, wherein a total number of working electrodes is greater than a total number of reference electrodes; and a controller coupled to the one or more reference electrodes and the two or more working electrodes, the controller configured to measure a voltage potential between at least one of the two or more working electrodes and at least one of the one or more reference electrodes.

According to another aspect of the present disclosure, a method of testing a test liquid is provided. The method comprises providing a flow channel, two or more working electrodes located in the flow channel, one or more reference electrodes located in the flow channel, wherein a total number of working electrodes is greater than a total number of reference electrodes; flowing a test liquid through the flow channel; and measuring one or more voltage potentials between the one or more reference electrodes and the two or more working electrodes.

Still other aspects, features, and advantages of the present disclosure may be readily apparent from the following detailed description by illustrating a number of example embodiments and implementations. The present disclosure may also be capable of other and different embodiments, and its several details may be modified in various respects, all without departing from the scope of the present disclosure. Further features and aspects of embodiments will become more fully apparent from the following detailed description, the claims, and the accompanying drawings. Accordingly, the drawings and description are to be regarded as illustrative in nature, and not as restrictive. The disclosure is to cover all modifications, equivalents, and alternatives falling within the scope of the claims.

BRIEF DESCRIPTION OF THE DRAWINGS

The accompanying drawings, described below, are for illustrative purposes and are not necessarily drawn to scale. The drawings are not intended to limit the scope of the disclosure in any way. Like numerals are used throughout the specification and drawings to denote like elements.

DETAILED DESCRIPTION

Figure 1A:
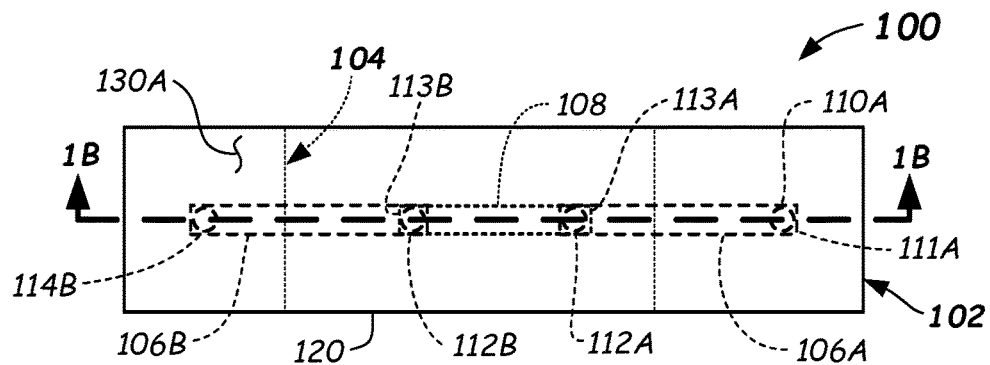
FIG. 1A illustrates a top plan view of a sensor assembly according to one or more embodiments of the disclosure.

In some chemical tests, it may be desirable to test for more than one constituent in a test liquid (e.g., a bio-liquid specimen) at a time. For example, a sensor assembly that can test for eight or more different constituents at a time is desirable. Moreover, in some instances the available volume of the test liquid (e.g., blood serum or plasma or other bio-liquid) to be tested may be quite small, such as when taken from, for example, a neonatal patient. Neonatal patient as used herein means an infant of less than 28 days of age. In certain instances, it may be desirable to not only test for multiple constituents at one time in one sensor assembly because but the available volume of test liquid available for the tests may be relatively small in volume, such as less than 100 µl or even less than 50 µl in some embodiments, for example.

Prior art sensor assemblies include chemical sensors, such as potentiometric sensors that measure the concentrations of specific chemical constituents in a test liquid. Each of the potentiometric sensors includes a reference electrode and a working electrode. A charge that is proportional to a constituent being measured develops on each of the working electrodes. By measuring the electric potential between the reference electrode and the working electrode of each potentiometric sensor, the concentration of the different constituents can be measured.

As described above, each potentiometric sensor in the prior art sensor assemblies includes two electrodes, the working electrode and the reference electrode. Thus, a sensor assembly that measures the concentrations of four constituents, for example, has eight electrodes. The sensor assemblies described herein include a common reference electrode that is associated with two or more working electrodes. Therefore, a sensor assembly that measures the concentrations of four constituents may have as few as five electrodes. It follows that the cumulative sensor sizes of the sensor assemblies described herein may be smaller than the cumulative sensor sizes of prior art sensor assemblies. The smaller cumulative sensor sizes described herein enable the sizes of the sensor assemblies described herein to be smaller than prior art sensor assemblies. As a result, the volume of test liquid used by the sensor assemblies described herein may be less than the volume of test liquid used in prior art sensor assemblies. In addition, the working electrodes may be arranged to face each other, which concentrates the working electrodes in smaller areas. This working electrode arrangement may further reduce the sizes of the sensor assemblies and the volume of test liquid used in the sensor assemblies.

Some reference electrodes in conventional sensor assemblies may interfere with their working electrodes. For example, the reference electrodes may emit small traces of chemicals that may interfere with the working electrodes. Some embodiments of the sensor assemblies described herein include one or more primary flow channels spaced from a secondary flow channel. The primary flow channels may each contain one or more working electrodes and the secondary flow channel may contain the reference electrode. Accordingly, the reference electrode is spaced a distance from the working electrodes, which may reduce the interference. In some embodiments, the reference electrode is located downstream of the working electrodes, which may further reduce the probability of the reference electrode interfering with the working electrodes. In some embodiments the secondary flow channel, including the reference electrode, is (vertically) offset from the primary flow channels, so the reference electrode is further spaced from the working electrodes.

Accordingly, in one aspect, an improved sensor assembly is provided that enables the carrying out of liquid testing (e.g., bio-liquid specimen testing) of multiple constituents simultaneously. In another aspect, the liquid testing can be carried out in some embodiments while utilizing a relatively small volume of the test liquid, such as when the test liquid comes from a neonatal patient. These and other aspects and features of the present disclosure will be described with reference to FIGS. 1A-4 herein.

In accordance with a first embodiment of the disclosure, as best shown in FIGS. 1A-1F and 4, sensor assemblies 100, 400 are provided. The sensor assemblies 100, 400 are configured to enable liquid testing (e.g., bio-liquid specimen testing). In some embodiments, the bio-liquid specimen testing can be while using only a small volume of the test liquid, although the bio-liquid specimen testing by the sensor assemblies 100, 400 can also be used for adult patients. Although the present disclosure is generally focused on microfluidics and testing small volumes of test liquids (e.g., bio-liquids), the present disclosure is applicable to testing of other volumes of test liquids as well as testing for the presence of and/or concentration of multiple constituents in non-bio-liquid specimens.

Figure 1B:
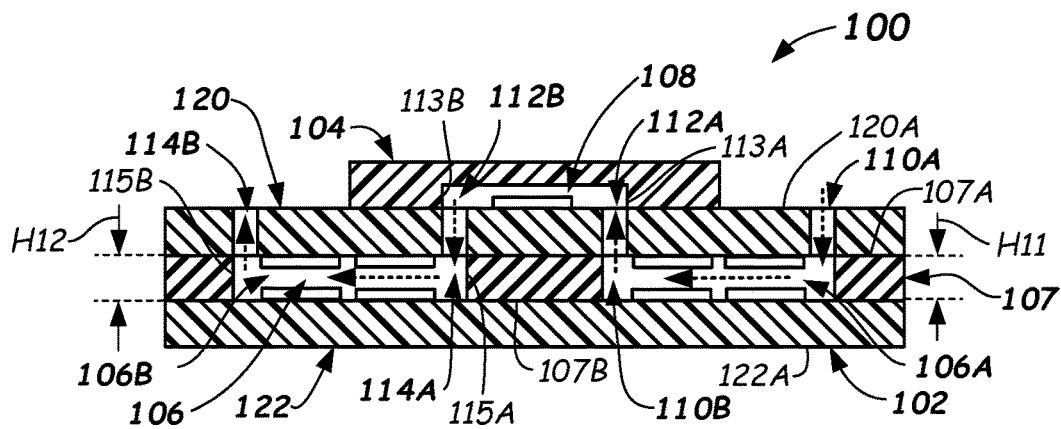
FIG. 1B illustrates a cross-sectioned side view of a sensor assembly taken along section line 1B-1B of FIG. 1A illustrating an example construction of primary and secondary channels within the sensor assembly according to one or more embodiments of the disclosure.
Figure 1C:
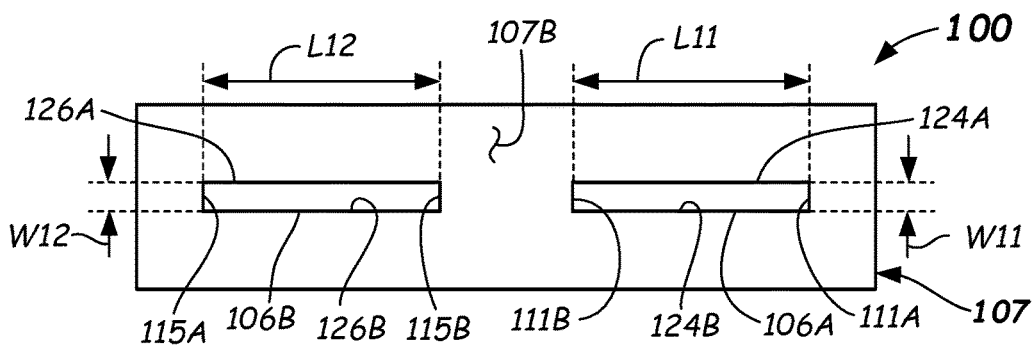
FIG. 1C illustrates a top plan view of an intermediate layer of a sensor assembly according to one or more embodiments of the disclosure.
Figure 1D:
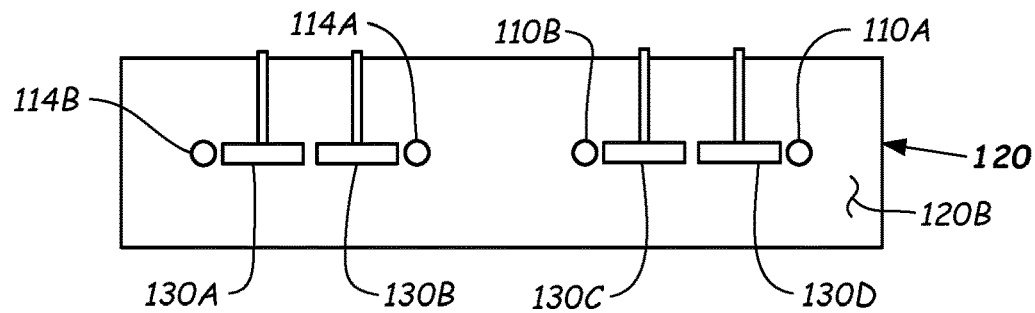
FIG. 1D illustrates a bottom plan view of a first layer of a sensor assembly according to one or more embodiments of the disclosure.
Figure 1E:
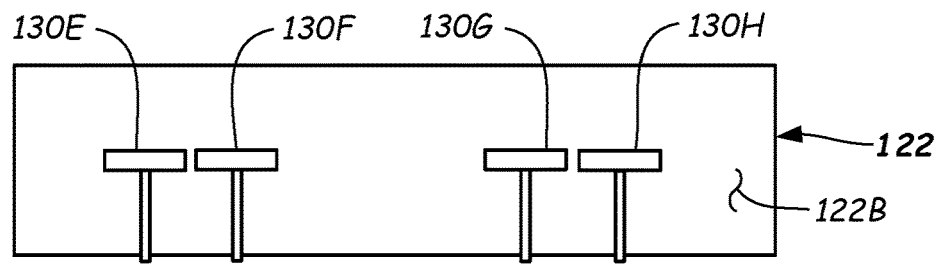
FIG. 1E illustrates a top plan view of a second layer of a sensor assembly according to one or more embodiments of the disclosure.

Reference is now made to FIGS. 1A, 1B, and 1C. FIG. 1A illustrates a top plan view of an embodiment of the sensor assembly 100. FIG. 1B illustrates a cross-sectioned side view of an embodiment of the sensor assembly 100 taken along section line 1B-1B of FIG. 1A. FIG. 1C illustrates an intermediate layer of the sensor assembly 100. The sensor assembly 100 includes a primary body 102 and a secondary body 104 that may be coupled together. The primary body 102 includes one or more primary channels that enable a test liquid to flow through the primary body 102. The embodiments described herein may include a flow channel 106 including a first primary channel 106A and a second primary channel 106B located within and formed in part by an intermediate layer 107 described below. The secondary body 104 includes a secondary channel 108 that is connected to and fluidly coupled in use to one or more of the first primary channel 106A and the second primary channel 106B. The first primary channel 106A may be referred to as a first flow channel portion, the secondary channel 108 may be referred to as a second flow channel portion, and the second primary channel 106B may be referred to as a third flow channel portion. The first primary channel 106A includes a first primary inlet 110A that may be located proximate a first end 111A of the first primary channel 106A. A first primary outlet 110B may be located proximate a second end 111B of the first primary channel 106A. The first primary inlet 110A may be configured to couple to the test liquid source, such as an inlet channel 354 (FIG. 3) formed in or as a part of the testing equipment the sensor assembly 100 is operative with. The inlet channel 354 can supply a test liquid 353 (e.g., bio-liquid specimen) from a reservoir 355 (FIG. 3) to be tested by the sensor assembly 100. Any suitable pump 356 may be provided to transfer the test liquid 353 from the reservoir 355 through the inlet channel 354 and into the first primary inlet 110A of the sensor assembly 100.

The first primary outlet 110B may be connected and coupled to a secondary channel inlet 112A located proximate a first end 113A of the secondary channel 108. The secondary channel 108 may include a secondary channel outlet 112B located proximate a second end 113B of the secondary channel 108. The secondary channel outlet 112B may be connected and coupled to a second primary inlet 114A located proximate a first end 115A of the second primary channel 106B. A second primary outlet 114B may be located proximate a second end 115B of the second primary channel 106B. The second primary outlet 114B may be configured to be connected and coupled to an outflow channel 357 that can be connected to a receptacle (e.g., waste receptacle 358, FIG. 3) that collects the test liquid 353 being expelled from the sensor assembly 100 after testing is completed.

A liquid flow path extends through the sensor assembly 100 between the first primary inlet 110A and the second primary outlet 114B as shown by the dotted arrows in FIG. 1B. The first primary inlet 110A may be coupled to a source of a test liquid (e.g., test liquid 353, FIG. 3). The test liquid 353 enters the sensor assembly 100 via the first primary inlet 110A, where the test liquid flows through the first primary channel 106A. The test liquid 353 exits the first primary channel 106A at the first primary outlet 110B and enters the secondary channel 108 via the secondary channel inlet 112A. The test liquid 353 then flows through the secondary channel 108 and exits via the secondary channel outlet 112B to the second primary inlet 114A. The test liquid 353 then flows through the second primary channel 106B to the second primary outlet 114B where the test liquid 353 exits the sensor assembly 100 through outflow channel 357.

As shown in FIG. 1B, the channels have end barriers that cause the test liquid to transition between the first primary channel 106A, the secondary channel 108, and the second primary channel 106B. As shown, the secondary channel 108 is located on a plane that is different than planes where at least one of the first primary channel 106A and the second primary channel 106B are located. In some embodiments, the first primary channel 106A and the second primary channel 106B may be located on the same plane. In other embodiments, the first primary channel 106A and the second primary channel 106B may be located on different planes. In other embodiments, the first primary channel 106A, the second primary channel 106B, and the secondary channel 108 may all be located on different planes. The transition between the plane of the secondary channel 108 and a plane of at least one of the first primary channel 106A and the second primary channel 106B may constitute the physical barrier between the secondary channel 108 and at least one of the first primary channel 106A and the second primary channel 106B.

The primary body 102 may include three layers as shown, including a first layer 120, a second layer 122, and the intermediate layer 107. Additional reference is made to FIG. 1D, which illustrates a bottom plan view of the first layer 120. Additional reference is also made to FIG. 1E, which illustrates a top plan view of the second layer 122. The first layer 120 includes an outer side 120A and an inner side 120B. The second layer 122 also includes an outer side 122A and an inner side 122B. The intermediate layer 107 includes a first side 107A and a second side 107B. The inner side 120B of the first layer 120 may be bonded to or otherwise fastened to the first side 107A of the intermediate layer 107 so as to form a sealed interface there between. The inner side 122B of the second layer 122 may be bonded to or otherwise fastened to the second side 107B of the intermediate layer 107 so as to form a sealed interface there between. The secondary body 104 may be coupled to or otherwise fastened to the outer side 120A of the first layer 120 so as to form a sealed interface there between.

The intermediate layer 107 may be formed from a gasket-type material. For example, the intermediate layer 107 may be impermeable to liquids that flow between the first primary inlet 110A and the second primary outlet 114B. The intermediate layer 107 may seal with the inner side 120B of the first layer 120 and the inner side 122B of the second layer 122 so as to prevent liquids from leaking from the sensor assembly 100.

As shown in FIG. 1C, the intermediate layer 107 may have portions of the first primary channel 106A and the second primary channel 106B formed therein. For example, the first primary channel 106A and the second primary channel 106B may extend fully between the first side 107A and the second side 107B of the intermediate layer 107. The first primary channel 106A can be elongated having a length L11 extending between the first end 111A and the second end 111B. The first primary channel 106A has a width W11 extending between a first side 124A and a second side 124B. The second primary channel 106B can be elongated having a length L12 extending between the first end 115A and the second end 115B. The second primary channel 106B has a width W12 extending between a first side 126A and a second side 126B. In some embodiments, the width W11 may be approximately the width of at least one of the first primary inlet 110A and the first primary outlet 110B. In some embodiments, the width W12 may be approximately the width of at least one of the second primary inlet 114A and the second primary outlet 114B.

The first primary channel 106A may have a height H11 (FIG. 1B) extending between the inner side 120B of the first layer 120 and the inner side 122B of the second layer 122. The second primary channel 106B may have a height H12 extending between the inner side 120B of the first layer 120 and the second side 132B of the second layer 122. In some embodiments, the height H11 and/or the height H12 may be approximately the thickness of the intermediate layer 107. In some embodiments, the height H11 may be approximately the same as the height H12.

In some embodiments, the length L11 of the first primary channel 106A may be equal to the length L12 of the second primary channel 106B. In some embodiments at least one of the length L11 and the length L12 may be in a range from 8 mm to 16 mm each, for example. In some embodiments, the width W11 may be equal to the width W12. In some embodiments at least one of the width W11 and the width W12 may be in a range from 0.056 mm to 0.94 mm, for example. In some embodiments, the height H11 and the height H12 can be in the range from 0.38 mm to 0.63 mm, for example. In some embodiments, the height H11 may be equal to the height H12. The secondary channel 108 may have dimensions equal to or approximate the dimensions of at least one of the first primary channel 106A and the second primary channel 106B. In some embodiments, the length of the secondary channel 108 may be shorter than at least one of the first primary channel 106A and the second primary channel 106B. Other suitable dimensions can be used.

Figure 1F:
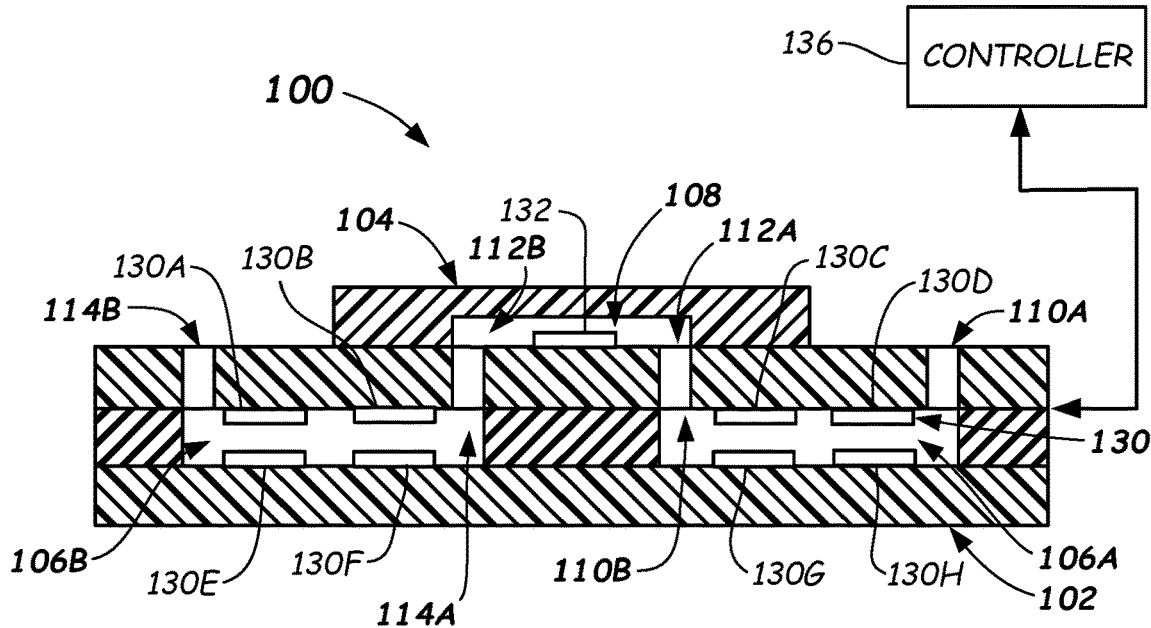
FIG. 1F illustrates a side cross-sectioned side view of a sensor assembly with some components removed according to one or more embodiments of the disclosure.

Additional reference is made to FIG. 1F, which illustrates a side cross-sectioned view of the sensor assembly 100 with some components removed and or not referenced for illustration purposes. The sensor assembly 100 may include one or more working electrodes 130A-130H and at least one reference electrode 132 that form one or more sensors, such as potentiometric sensors. For example, the reference electrode 132 forms at least one potentiometric sensor with at least one of the working electrodes 130A-130H. In the depicted embodiment of FIG. 1E, the sensor assembly 100 include eight working electrodes 130, which are referred to individually as working electrodes 130C-130D and 130G-130H. The working electrodes 130C-130D and 130G-130H located in the first primary channel 106A may be referred to as the first working electrodes and the working electrodes 130A-130B and 130E-130F located in the second primary channel 106B may be referred to as the second working electrodes. The sensor assembly 100 may include different numbers of working electrodes 130. The working electrodes 130 may be made of any suitable conductive material, such as metal foil, conductive ink, or the like, and combinations thereof.

A controller 136 may be electrically coupled to the working electrodes 130A-130H and also the reference electrode 132. In some embodiments, the controller 136 may supply a reference voltage to the reference electrode 132. The controller 136 may measure respective voltage potentials between each of the individual working electrodes 130A-130H and the reference electrode 132. Based on the voltage potentials, the controller 136 may determine the concentration of specific analytes or chemical constituents in the test fluid 353 as described below.

Figure 2:
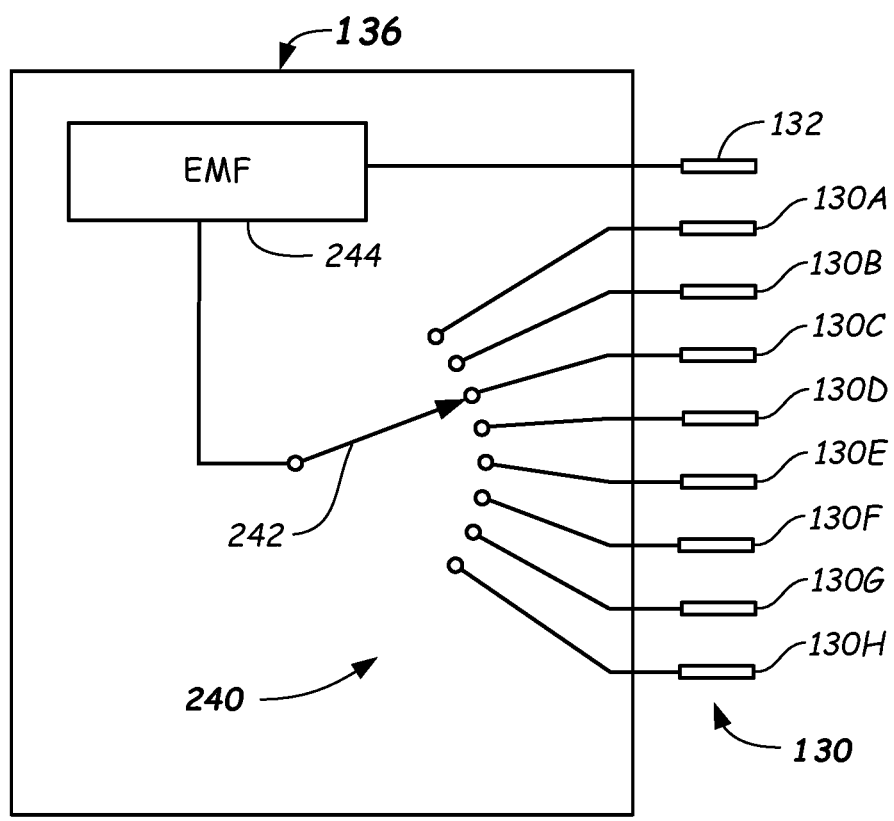
FIG. 2 illustrates a schematic diagram of a circuit that measures voltage potential(s) between one or more working electrodes and a reference electrode in a sensor assembly according to one or more embodiments of the disclosure.

Additional reference is made to FIG. 2, which illustrates an example embodiment of a circuit 240 within the controller 136 that may be utilized to measure the potential voltages (the electro-motive force (EMF)) between each of the working electrodes 130A-130H and the reference electrode 132. The circuit 240 may include a switching device 242, such as an electronic switch that selectively couples one or more working electrodes 130A-130H to a voltage measuring device 244. The voltage measuring device may be any suitable device that operates to measure the voltage potential (EMF) between the selected working electrodes 130A-130H and the reference electrode 132.

As described above, the working electrodes 130A-130H and the reference electrode 132 may form potentiometric sensors. Potentiometric sensors are a type of chemical sensor that may be used to determine the concentration of some components of a gas or a liquid. Potentiometric sensors measure the electrical potential between a respective working electrode 130A-130H and the reference electrode 132 when no current is conducting between the working electrodes 130 and the reference electrode 132. Thus, each of the individual working electrodes 130A-130H may be an individual potentiometric sensor referenced to the common reference electrode 132. A single reference electrode is shown. However, in some embodiments a first reference sensor may be configured to be used with a first grouping of working electrodes and a second reference sensor may be configured to be used with a second grouping of working electrodes.

Each of the working electrodes 130A-130H may include a membrane or the like including a particular selective reagent that reacts with a specific analyte in the test liquid 353. For example, the membrane can react with specific analytes such as sodium, potassium, calcium, or chloride. These reactions accumulate charges on the working electrodes 130, which then can be measured as electric potentials between the individual working electrodes 130A-130H and the reference electrode 132. The amount of charge accumulated on a working electrode is proportional to the analyte concentration in the test liquid 353, which is proportional to the potential between the respective working electrode 130A-130H and the reference electrode 132. The potential of a potentiometric sensor is based on the Nernst equation (1), which predicts a linear dependence of the potential, E, on the logarithm of a function of the activity of specific ions the test solution as follows:

$$E = E° + \frac{RT}{nF}\ln a_i \quad (1)\text{ Nernst Equation}$$

where E is the potential between the working electrode and the reference electrode 132, R is the gas coefficient (8.314 J/K), F is the faraday constant (96,500 C/mol), n is the number of electrons, and $a_i$ is the activity of the ion being detected. E° is a potential applied to the reference electrode 132. The controller 136 may calculate the concentration of an analyte in the test liquid 353 based on the Nernst equation.

The potentials of different working electrodes 130A-130H may be measured relative to the reference electrode 132 to measure concentrations of specific analytes within the test liquid 353. Different analytes may be measured by different ones of the working electrodes. For example each working electrode 130A-130H may include a different selective reagent applied thereto, so that a large number of analytes can be tested on the test liquid 253.

In some embodiments, the working electrodes 130A-130H may be grouped to form microsensors that may measure microsamples in the test liquid 353. For example, the working electrodes 130A, 130B, 130E, and 130F, which are downstream from the reference electrode 132 may constitute a first microsensor. The working electrodes 130C, 130D, 130G, and 130H, which are upstream of the reference electrode 132 may constitute a second microsensor. The working electrodes 130B, 130C, 130F, and 130G, which are located closest to the reference electrode 132 may constitute a third microsensor. Other arrangements of the working electrodes 130 may form other microsensors.

The working electrodes in the first primary channel 106A may be referred to as the first working electrodes and the working electrodes in the second primary channel 106B may be referred to as the second working electrodes. At least one of the first working electrodes and the second working electrodes may include a first working electrode and a second working electrode, wherein the first working electrode faces the second working electrode across the first primary channel 106A. For example, referring to FIG. 1F, the working electrode 130C faces the working electrode 130G. In some embodiments, the first working electrode and the second working electrode are located on opposite sides of at least one of the first primary channel 106A and the second primary channel 106B. In some embodiments, the first working electrodes and/or the second working electrodes include two or more working electrodes arranged along a length of the first primary channel 106A and/or the second primary channel 106B. In some embodiments, the first working electrodes include a first array of working electrodes arranged along a length of the first primary channel 106A and a second array of working electrodes arranged along a length of the first primary channel 106A, wherein the first array of working electrodes faces the second array of working electrodes. Such an arrangement is shown by the working electrodes 130C, 130D, 130G, and 130H. The same arrangement may apply to the second primary channel 106B.

Some reference electrodes in conventional sensor assemblies interfere with their working electrodes. For example, the reference electrodes may emit small traces of chemicals that may interfere with the working electrodes 130. Secondary channel 108 described herein includes the reference electrode 132 contained therein. Accordingly, the reference electrode 132 is spaced a distance from the working electrodes 130C-130D and 130G-130H located upstream from the reference electrode 132, which reduces the probability of the reference electrode 132 interfering with these working electrodes 130C-130D and 130G-130H. In addition, by offsetting the secondary channel 108 including the reference electrode 132 from the first primary channel 106A and/or the second primary channel 106B, the reference electrode 132 is further spaced from the working electrodes 130, as they are located in different planes.

Conventional sensor assemblies using potentiometric sensors include a reference electrode and a working electrode for every potentiometric sensor. Accordingly, every sensing location in conventional sensor assemblies consume relatively large areas. Sensing in the sensor assembly 100 is performed by each of the working electrodes 130A-130H in conjunction with the single reference electrode 132 that is spaced from the location of the working electrodes 130A-130H. Accordingly, the sensing locations of the sensor assembly 100 may be much smaller than the sensing locations of conventional sensor assemblies. Optionally, they may be made larger to possibly improve signal strength.

For example, a sensing location may only include a working electrode. Thus the sensing location may be much smaller than in conventional potentiometric sensors. Thus, the flow channel 106 in which test liquid 353 flows within the sensor assembly 100 may be smaller than those in conventional sensor assemblies. Although the sensor assembly 100 includes the secondary channel 108, the overall volume of the secondary channel 108, the first primary channel 106A, and the second primary channel 106B may be less than the volume of channels in conventional sensor arrays because the sensing locations may be smaller. For example, volume of the first primary channel 106A, the second primary channel 106B, and the secondary channel 108 can be less than 100 µl, or from 50 µl to 100 µl in some embodiments. The first primary channel 106A, the second primary channel 106B, and the secondary channel 108 can have other volumes.

The sensor assembly 100 can be configured to test for a concentration of a constituent in various types of the test liquid 353. For example, the test liquid can be a bio-liquid selected from a group of whole blood, blood serum or plasma, urine, cerebrospinal fluid (CSF), dialysate, serous fluid (such as pleural fluid, pericardial fluid, and peritoneal fluid), interstitial fluid, synovial fluid, intraocular fluid, lymph plasma, digestive fluid, and human tissue-containing liquid. Other bio-liquids and other types of non-bio-liquids can be tested. In other embodiments, the sensor assembly 100 can be configured to test for concentrations of two or more constituents contained in the test liquid 353 flowing through the flow channel 106.

Figure 3:
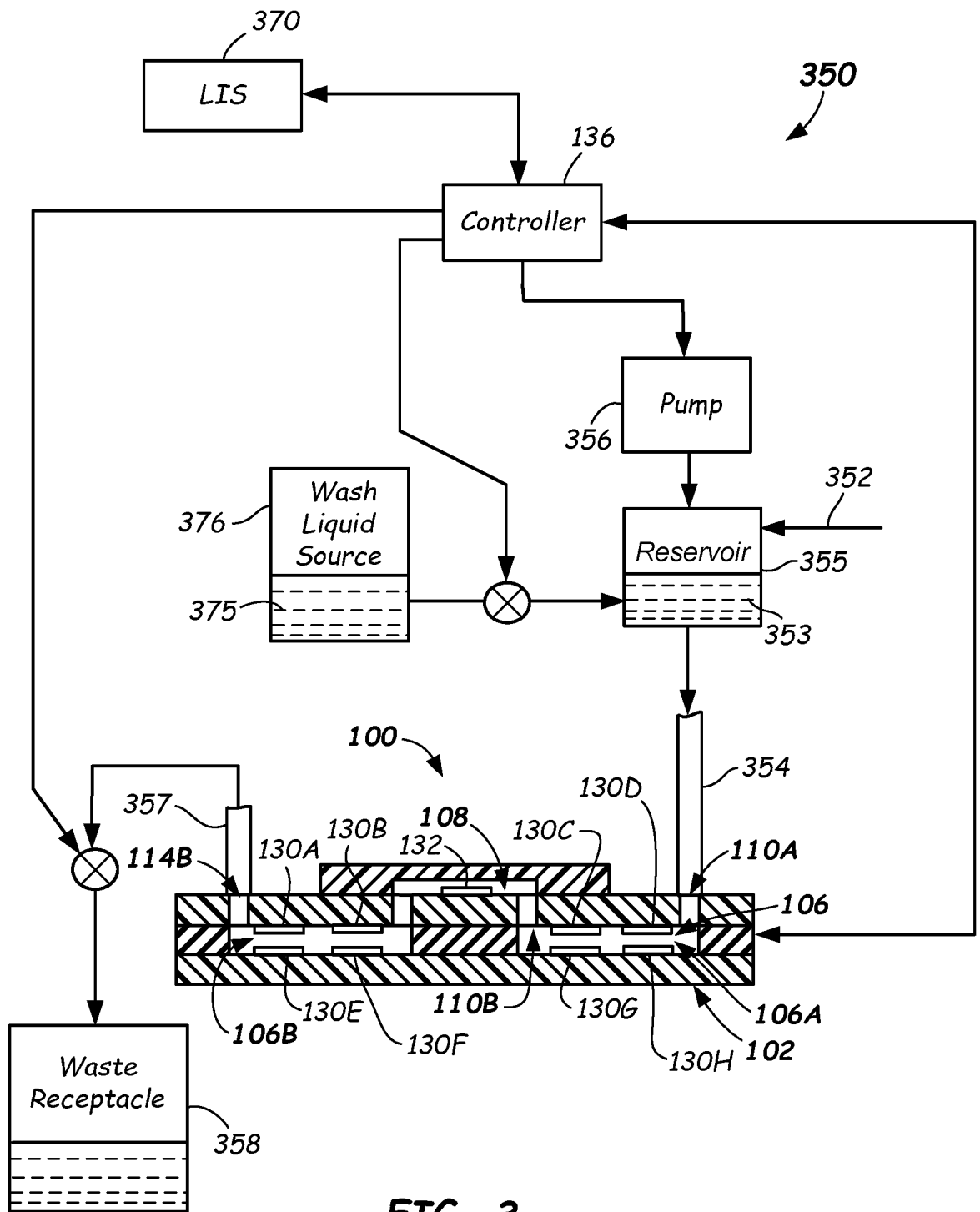
FIG. 3 illustrates a schematic diagram of a liquid testing apparatus including an embodiment of a sensor assembly including primary and secondary channels according to one or more embodiments of the disclosure.

In FIG. 3, an embodiment of a liquid testing apparatus 350 utilizing a sensor assembly 100 including one or more primary channels 106A, 106B and a secondary channel 108 is illustrated. The sensor assembly 100 used in this embodiment can be positioned in a horizontal orientation as shown. Other orientations are possible. In operation, the reservoir 355 can receive a test liquid 353 by any suitable means. For example, the test liquid 353 can be injected therein (indicated by arrow 352), such as by a syringe or other injection mechanism coupleable to the reservoir 355. A pump 356 coupled to or operative within the reservoir 355, such as a pressure pump, piston pump, or the like, can be actuated via control signals from the controller 136. As a result, some, or all, of the test liquid 353 is moved by the pump 356. Any suitable liquid moving system can be used.

The test liquid 353 then flows through inlet channel 354 and into the first primary inlet 110A. One or more valves may be included in the channel or associated with the pump 356 to control the extent of flow and to stop flow as desired. In other embodiments, the pump 356 is precise and can control the flow volume precisely.

With additional reference FIG. 1B, the test liquid 353 flows through the first primary channel 106A into the secondary channel inlet 112A, through the secondary channel 108, into the second primary inlet 114A, through the second primary channel 106B, and out the second primary outlet 114B. As the test liquid 353 flows through the first primary channel 106A and the second primary channel 106B, the test liquid 353 contacts each of the working electrodes 130A-130H. As the test liquid 353 flows through the secondary channel 108, the test liquid 353 contacts the reference electrode 132.

The tests can be run and the analyte measurements can be obtained from each of the working electrodes 130A-130H in combination with the reference electrode 132 by communication with the controller 136 and by way of conventional computations. The controller 136 may be communicatively coupled to a laboratory information system (LIS) 370, for example, so that analyte concentrations from the test can be promptly sent to the originator/requestor or elsewhere.

Following each test, a valve (not shown) can be opened to flow a wash liquid 375 from a wash liquid source 376 to and through the reservoir 355, inlet channel 354 and the sensor assembly 100 and finally to a waste receptacle 358. The primary channels 106A, 106B and the secondary channel 108 receiving the wash liquid 375 cleans and readies the sensor assembly 100 for the next test on a new test liquid 353. Multiple washes may be undertaken in some embodiments.

Figure 4:
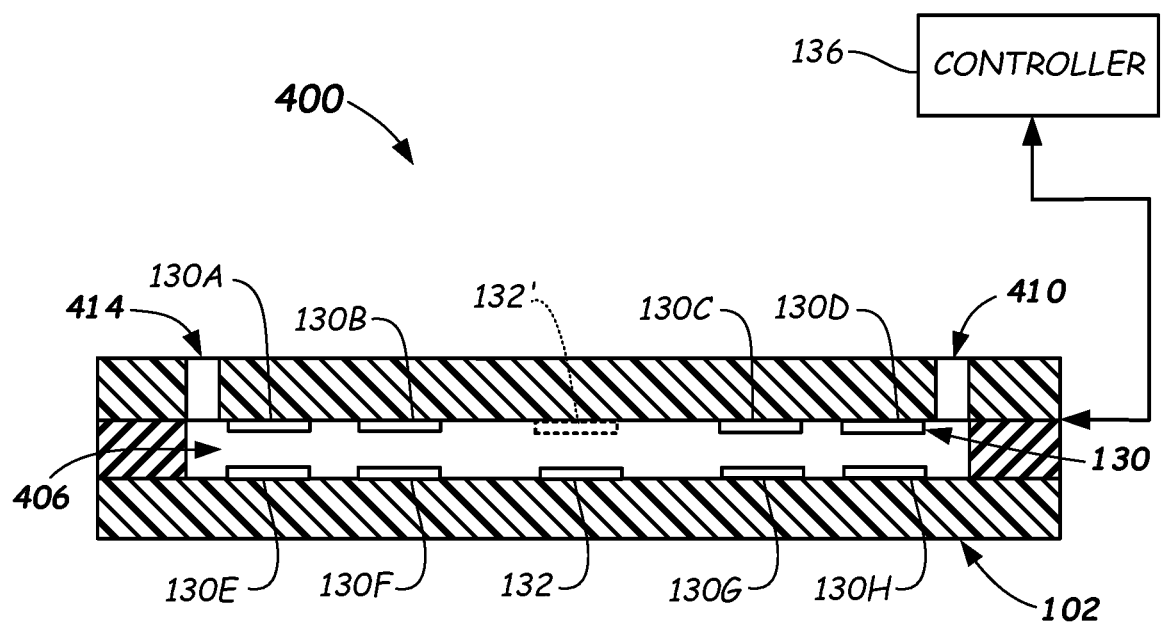
FIG. 4 illustrates a cross-sectioned side view of a sensor assembly illustrating an example construction of a flow channel within the sensor assembly according to one or more embodiments of the disclosure.

Another embodiment of a sensor assembly 400 is illustrated in FIG. 4. The sensor assembly 400 includes a continuous flow channel 406 that may be located on a single plane and that may be straight between an inlet 410 and an outlet 414. The flow channel 406 may be formed in the same or similar manner as the first primary channel 106A and the second primary channel 106B. The inlet 410 may function in the same or similar manner as the first primary inlet 110A of FIG. 1B and the outlet 414 may function in the same or similar manner as the second primary outlet 114B of FIG. 1B. In some embodiments, the dimensions of the sensor assembly 400 may be the same or substantially similar to the dimensions of the primary body 102 (FIG. 1B) of the sensor assembly 100.

The sensor assembly 400 may include the reference electrode 132 and two or more working electrodes 130. In some embodiments, the sensor assembly 400 includes one or more reference electrodes, wherein a number of working electrodes is greater than a number of reference electrodes. The reference electrode 132 may be common to two or more of the working electrodes 130. In some embodiments, one or more working electrodes may be located to a first side (e.g., the left side as shown in FIG. 4) and one or more electrodes may be located to a second side (e.g., the right side as shown in FIG. 4) of the reference electrode 132.

In some embodiments, the working electrodes 130 include a first working electrode (e.g., working electrode 130C) and a second working electrode (e.g., working electrode 130G), wherein the first working electrode faces the second working electrode. In some embodiments, the working electrodes 130 include a first working electrode (e.g., working electrode 130C) and a second working electrode (e.g., working electrode 130G), wherein the first working electrode faces the second working electrode, and wherein the first working electrode and the second working electrode are located on opposite sides of the flow channel 406.

In some embodiments, two or more working electrodes 130 are arranged along a length of the flow channel 406. In some embodiments, at least some of the working electrodes 130 constitute a first array of working electrodes (e.g., working electrodes 130C and 130D) arranged along a length of the flow channel 406. A second array of working electrodes (e.g., working electrodes 130G and 130H) is arranged along a length of the flow channel 406, wherein the first array of working electrodes faces the second array of working electrodes.

Figure 5:
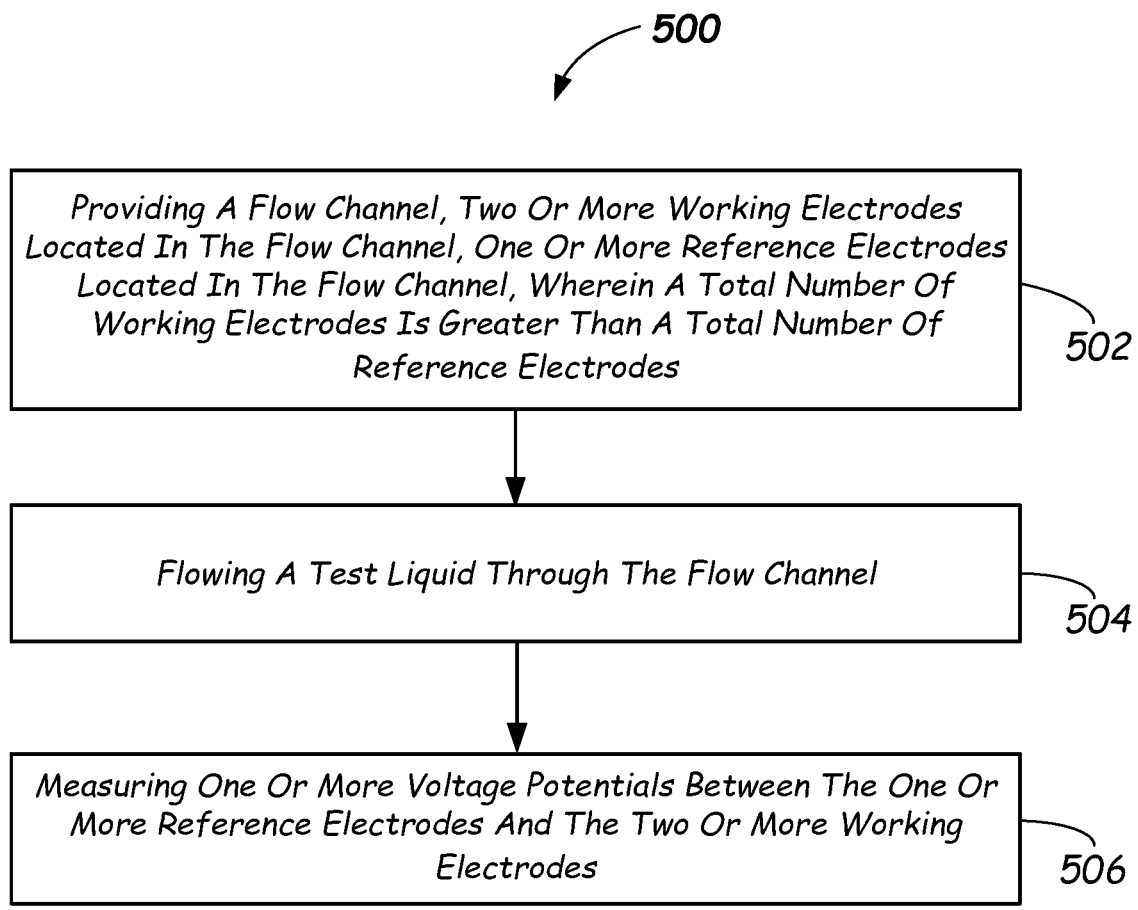
FIG. 5 illustrates a flowchart of a method of testing a test liquid according to one or more embodiments of the disclosure.

According to another aspect, a method of testing a test liquid 353 according to embodiments will now be described with reference to FIG. 5. The method 500 of testing a test liquid 353 includes, in 502, providing a flow channel (e.g., flow channel 406), one or more reference electrodes (e.g., reference electrode 132) located in the flow channel, and two or more working electrodes (e.g., working electrodes 130) located in the flow channel, wherein a total number of working electrodes is greater than a total number of reference electrodes. The method 500 further includes, in 504, flowing a test liquid (e.g., test liquid 353) through the flow channel. The method 500 further includes, in 506, measuring one or more voltage potentials between the one or more reference electrodes and the two or more working electrodes.

Following testing, the test liquid 353 is removed and a wash liquid (e.g., wash liquid 375) can be introduced to the inlet (e.g., inlet 410) to minimize traces of the test liquid 353 therein. Following the test and washing operations, another test of another test liquid, such as from another patient specimen can be conducted. Many tests can be conducted, such as 40 or more tests of different test liquids before the sensor assembly 100 is replaced with a new sensor assembly. In some embodiments, a calibrator liquid can be received in the first primary inlet 110A, such as before and after a series of tests.

Figure 6:
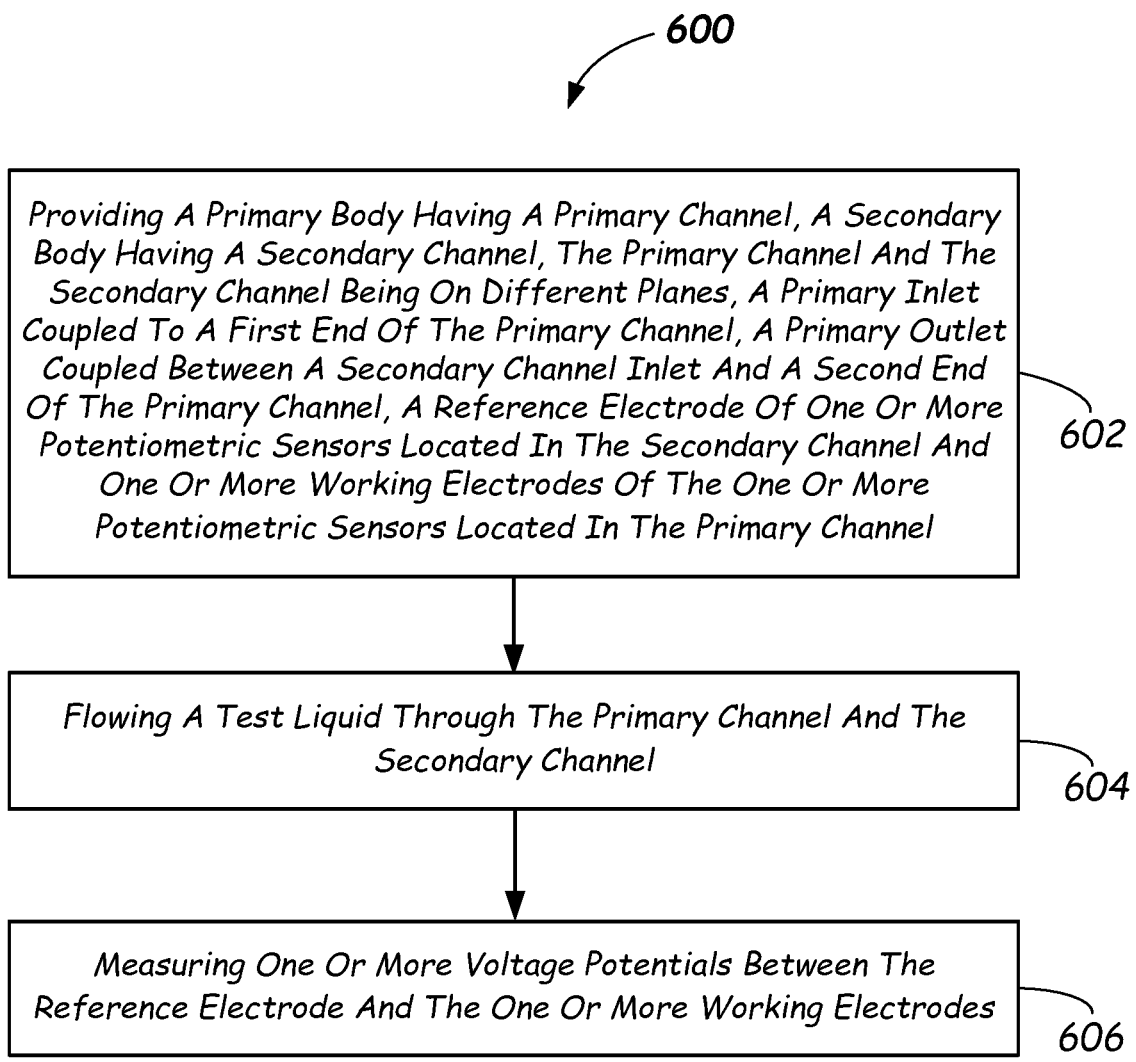
FIG. 6 illustrates a flowchart of another method of testing a test liquid according to one or more embodiments of the disclosure.

According to another aspect, a method 600 of testing a test liquid 353 according to embodiments will now be described with reference to FIG. 6. The method 600 of testing a test liquid 353 includes, in 602, providing a primary body (e.g., primary body 102) having a primary channel (e.g., first primary channel 106A and/or second primary channel 106B), a secondary body (e.g., secondary body 104) having a secondary channel (e.g., secondary channel 108), the primary channel and the secondary channel being located on different planes, a primary inlet (e.g., first primary inlet 110A) coupled to a first end (e.g., first end 111A) of the primary channel, a primary outlet (e.g., first primary outlet 110B) coupled between a secondary channel inlet (e.g., secondary channel inlet 112A) and a second end (e.g., second end 111B) of the primary channel, a reference electrode (e.g., reference electrode 132) of one or more potentiometric sensors located in the secondary channel and one or more working electrodes (e.g., working electrodes 130A-130H) of the one or more potentiometric sensors located in the primary channel.

The method 600 further includes, in 604, flowing a test liquid (e.g., test liquid 353) through the primary channel and the secondary channel. The method 600 further includes, in 606, measuring one or more voltage potentials between the reference electrode and the one or more working electrodes.

Additional Embodiments

In one or more additional apparatus embodiments, the primary body 102 may include a single primary channel, such as solely the first primary channel 106A. The single primary channel may be coupled to a secondary channel 108. In such an embodiment, the secondary channel outlet 112B may be the outlet of the sensor assembly 100. Accordingly, the secondary channel outlet 112B may be coupled to the waste receptacle 358.

In one or more additional apparatus embodiments, the sensor assembly 100 and/or the sensor assembly 400 may include one or more reference electrodes 132, wherein a number of working electrodes 130 is greater than a number of reference electrodes. In one or more additional apparatus embodiments, one or more working electrodes 130 may be located in the secondary channel 108. In some embodiments, one or more additional reference electrodes 132' could be provided in the flow channel 406, provided that a total number of reference electrodes 132, 132' are less than a total number of working electrodes 130.

While embodiments of this disclosure have been disclosed in example forms, many modifications, additions, and deletions can be made therein without departing from the scope of this disclosure, as set forth in the claims and their equivalents.

What is claimed is:

1. A sensor assembly, comprising:
   a flow channel;
   two or more working electrodes located in the flow channel;
   one or more reference electrodes located in the flow channel, wherein a total number of working electrodes is greater than a total number of reference electrodes;
   a primary body having a first flow channel portion of the flow channel;
   a secondary body having a second flow channel portion of the flow channel, the first flow channel portion and the second flow channel portion being on different planes;
   an inlet coupled to a first end of the first flow channel portion; and
   an outlet coupled to the second flow channel portion, wherein:
   at least one reference electrode is located in the second flow channel portion, and
   at least one of the two or more working electrodes is located in the first flow channel portion.

2. The sensor assembly of claim 1, wherein the two or more working electrodes include a first working electrode and a second working electrode, wherein the first working electrode faces the second working electrode.

3. The sensor assembly of claim 1, wherein the two or more working electrodes include a first working electrode and a second working electrode, wherein the first working electrode faces the second working electrode, and wherein the first working electrode and the second working electrode are located on opposite sides of the flow channel.

4. The sensor assembly of claim 1, wherein the two or more working electrodes are arranged along a length of the flow channel.

5. The sensor assembly of claim 1, wherein the two or more working electrodes comprise a first array of working electrodes arranged along a length of the flow channel and a second array of working electrodes arranged along a length of the flow channel, wherein the first array of working electrodes faces the second array of working electrodes.

6. The sensor assembly of claim 1, wherein one or more working electrodes are located on a first side of a reference electrode and one or more working electrodes are located on a second side of the reference electrode.

7. The sensor assembly of claim 1, wherein the two or more working electrodes and the one or more reference electrodes are configured to test for concentrations of two or more constituents contained in test liquid flowing through the flow channel.

8. The sensor assembly of claim 7, wherein the test liquid is a liquid selected from a group comprising: whole blood, blood serum or plasma, urine, cerebrospinal fluid, dialysate, serous fluid, interstitial fluid, synovial fluid, intraocular fluid, lymph plasma, digestive fluid, and human tissue-containing liquid.

9. The sensor assembly of claim 1, wherein two or more working electrodes are located in the first flow channel portion and include a first working electrode and a second working electrode, wherein the first working electrode faces the second working electrode, and wherein the first working electrode and the second working electrode are located on opposite sides of the first flow channel portion.

10. The sensor assembly of claim 1, wherein the one or more working electrodes include two or more working electrodes arranged along a length of the first flow channel portion.

11. The sensor assembly of claim 1, wherein the one or more working electrodes include a first array of working electrodes arranged along a length of the first flow channel portion and a second array of working electrodes arranged along a length of the first flow channel portion, wherein the first array of working electrodes faces the second array of working electrodes.

12. The sensor assembly of claim 1, further comprising:
the primary body including a first layer, a second layer, and an intermediate layer located between the first layer and the second layer, and wherein the first flow channel portion is formed in the intermediate layer; and
the secondary body attached to the first layer of the primary body, wherein the second flow channel portion is located in the secondary body.

13. The sensor assembly of claim 1, further comprising a third flow channel portion coupled to the outlet of the second flow channel portion, wherein at least one of the two or more working electrodes is located in the second flow channel portion.

14. A method of testing a test liquid, comprising:
providing the sensor assembly of claim 1;
flowing a test liquid through the flow channel; and
measuring one or more voltage potentials between the one or more reference electrodes and the two or more working electrodes.

15. A sensor assembly, comprising
a flow channel;
two or more working electrodes located in the flow channel;
one or more reference electrodes located in the flow channel, wherein a total number of working electrodes is greater than a total number of reference electrodes;
a body including a first layer, a second layer, and an intermediate layer located between the first layer and the second layer, wherein the flow channel is formed within the intermediate layer; and
an inlet that extends through the first layer and into the flow channel formed in the intermediate layer.

16. The sensor assembly of claim 15, wherein the intermediate layer is adhered to an inner side of the first layer and an inner side of the second layer.

17. The sensor assembly of claim 15, wherein the two or more working electrodes include a first working electrode and a second working electrode, wherein the first working electrode faces the second working electrode.

18. The sensor assembly of claim 15, wherein the two or more working electrodes include a first working electrode and a second working electrode, wherein the first working electrode faces the second working electrode, and wherein the first working electrode and the second working electrode are located on opposite sides of the flow channel.

19. The sensor assembly of claim 15, wherein the two or more working electrodes are arranged along a length of the flow channel.

20. A liquid testing apparatus, comprising:
a flow channel;
two or more working electrodes located in the flow channel;
one or more reference electrodes located in the flow channel, wherein a total number of working electrodes is greater than a total number of reference electrodes;
a body including a first layer, a second layer, and an intermediate layer located between the first layer and the second layer; wherein the flow channel is formed within the intermediate layer;
an inlet that extends through the first layer and into the flow channel formed in the intermediate layer; and
a controller coupled to the one or more reference electrodes and the two or more working electrodes, the controller configured to measure a voltage potential between at least one of the two or more working electrodes and at least one of the one or more reference electrodes.

* * * * *